United States Patent [19]
Gnegy

[11] Patent Number: 5,152,285
[45] Date of Patent: Oct. 6, 1992

[54] THERAPEUTIC BOOT FOR APPLYING HEAT OR COLD TO THE LEG OF A HORSE

[75] Inventor: Brian D. Gnegy, Arroyo Grande, Calif.

[73] Assignee: Hufmeister Aluminum Horseshoe Company, Arroyo Grande, Calif.

[21] Appl. No.: 811,014

[22] Filed: Dec. 20, 1991

[51] Int. Cl.$^5$ .............................................. A61F 7/00
[52] U.S. Cl. ...................................... 128/402; 54/82
[58] Field of Search ............... 128/379, 380, 382, 384, 128/394, 400, 402, 403; 62/530, 259.3; 602/12, 2, 13, 14; 54/82

[56] References Cited

U.S. PATENT DOCUMENTS

| | | | |
|---|---|---|---|
| 2,749,914 | 6/1956 | Braley | 128/402 |
| 2,842,655 | 7/1958 | Schwebel | 128/402 |
| 3,561,435 | 2/1971 | Nicholson | 128/402 |
| 3,710,075 | 1/1973 | Jablonski | 128/379 |
| 3,717,145 | 2/1973 | Berndt | 128/402 |
| 3,822,705 | 7/1974 | Pilotte | 128/379 |
| 3,882,867 | 5/1975 | Moran | 128/402 |
| 3,905,367 | 9/1975 | Darlich | 128/379 |
| 3,955,565 | 5/1976 | Johnson, Jr. | 602/12 |
| 4,139,004 | 2/1979 | Gonzalez | 128/400 |
| 4,688,572 | 8/1987 | Hubbard et al. | 128/400 |
| 4,793,149 | 12/1988 | Riche | 62/530 |
| 4,834,079 | 5/1989 | Benckhuijsen | 128/379 |
| 4,886,063 | 12/1989 | Crews | 128/403 |
| 4,964,402 | 10/1990 | Grilm et al. | 128/402 |
| 5,016,629 | 5/1991 | Kanare | 128/402 |
| 5,027,801 | 7/1991 | Grilm | 128/402 |

FOREIGN PATENT DOCUMENTS

| | | | |
|---|---|---|---|
| 2826353 | 12/1979 | Fed. Rep. of Germany | 128/402 |
| 2202447 | 9/1988 | United Kingdom | 128/400 |

*Primary Examiner*—Paul E. Shapiro
*Assistant Examiner*—Mark S. Graham
*Attorney, Agent, or Firm*—Donald A. Streck

[57] ABSTRACT

A boot system for selectively applying heat or cold to the lower portion of the leg of a horse for therapeutic purposes. There is a U-shaped inner boot portion positioned over the lower portion of the leg at a front portion thereof. The inner boot portion has a leather front panel with a pair of side panels extending from the front panel. It is lined with the fabric portion of a touch fastener material and has hook portion on the outer surface of the side panels. There is also a leather covered U-shaped outer boot portion positioned over the back of the leg with a pair of side panels overlapping the pair of side panels of the inner boot portion and lined with a fabric portion of the touch fastener material in releasable engagement with the hook portion on the outer surface of the pair of side panels of the inner boot portion. A plurality of pockets each having a hook portion of the touch fastener material on a surface thereof are releasably attached to the fabric portion of the touch fastener material at a point where heat or cold is to be applied to the lower portion of the leg. A plurality of gel-filled hot/cold packs are disposed within respective ones of the pockets.

9 Claims, 2 Drawing Sheets

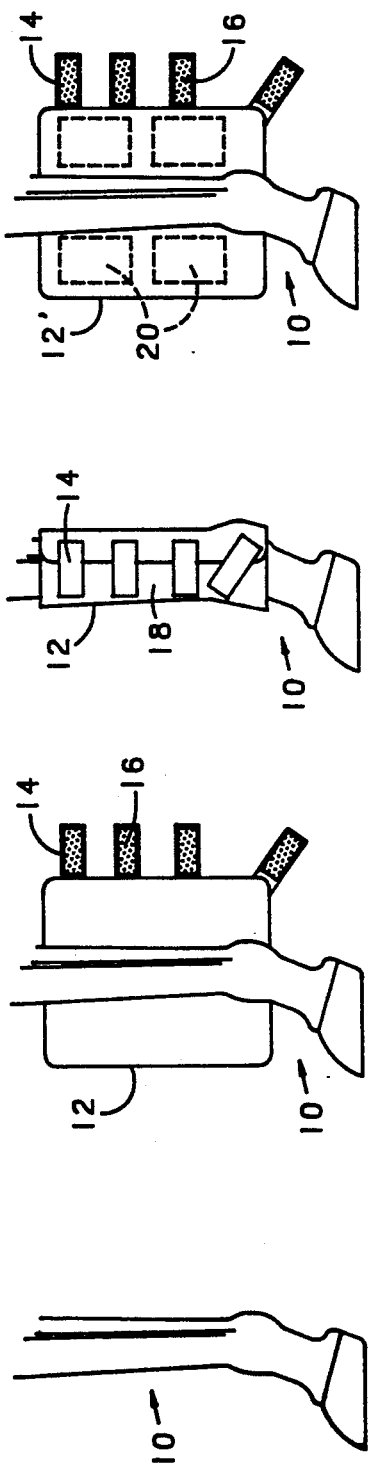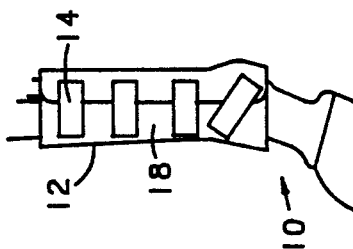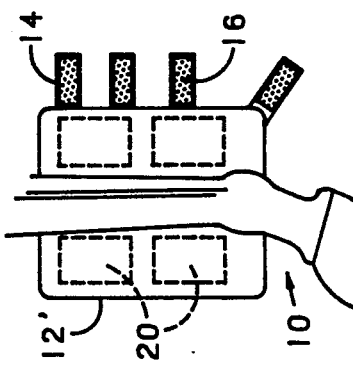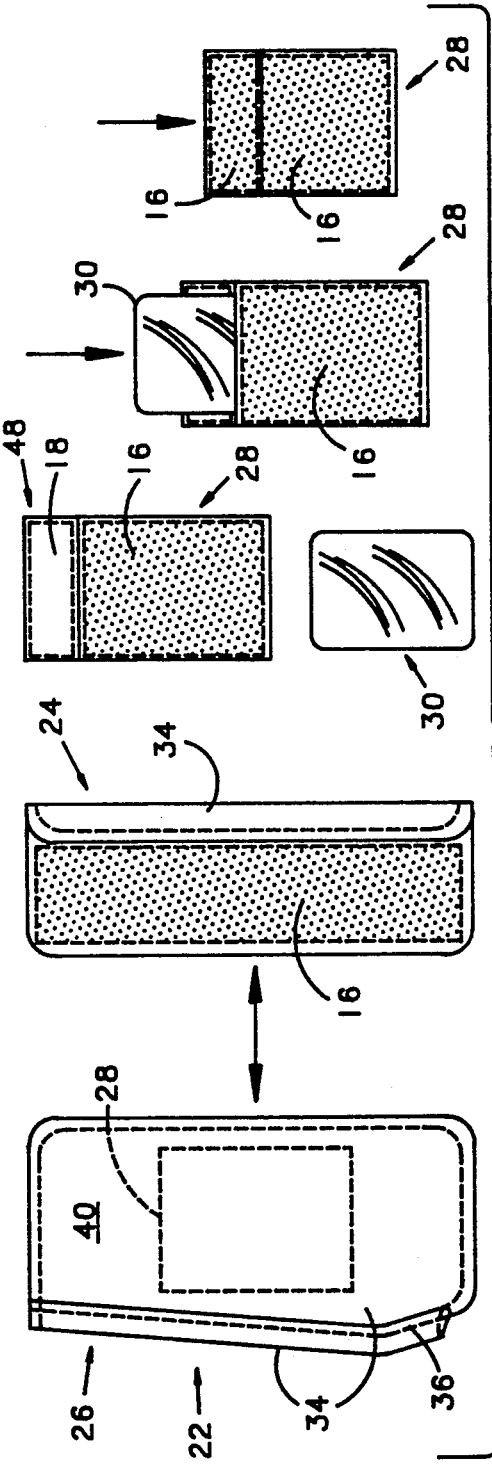

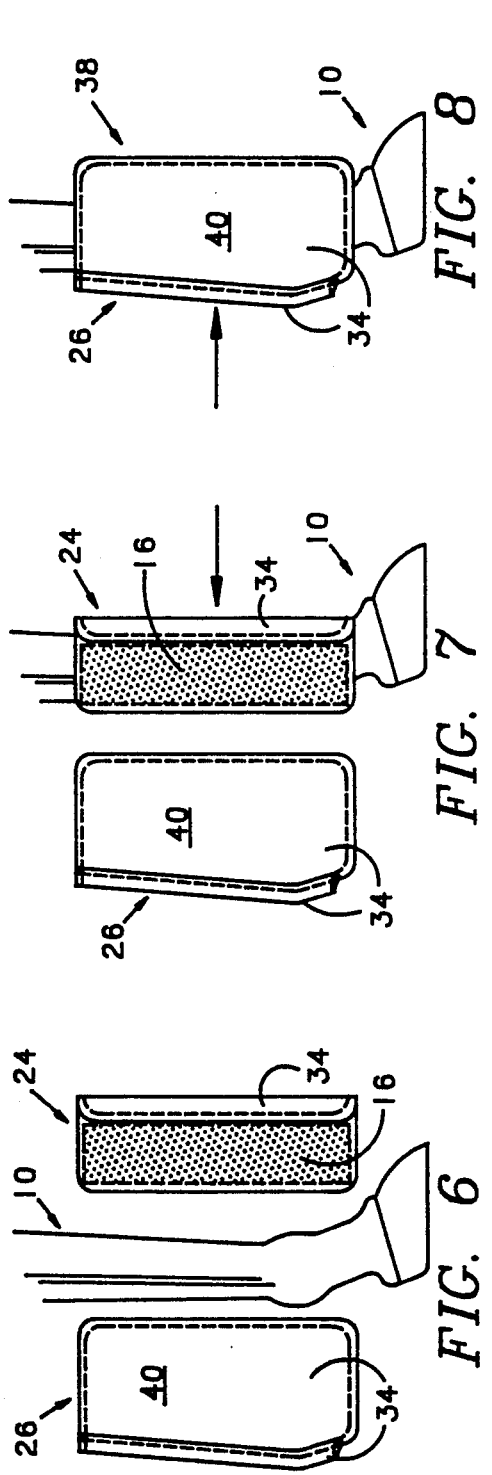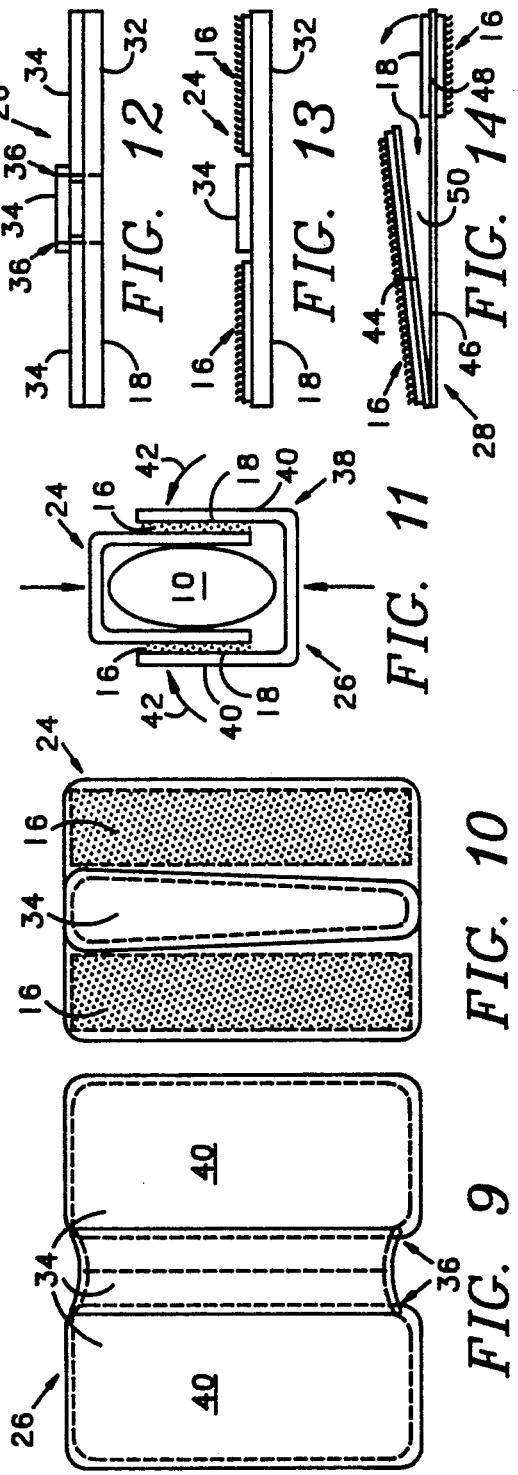

THERAPEUTIC BOOT FOR APPLYING HEAT OR COLD TO THE LEG OF A HORSE

BACKGROUND OF THE INVENTION

This invention relates to equine veterinary products and, more particularly, to a boot system for selectively applying heat or cold to the lower portion of the leg of a horse for therapeutic purposes comprising, a U-shaped inner boot portion positioned over the lower portion of the leg at a front portion thereof, the inner boot portion having a front panel of a material having the qualities of leather with a pair of side panels extending from the front panel along side edges thereof, the inner boot portion being lined with a fabric portion of a touch fastener material, the inner boot portion having a hook portion of the touch fastener material on an outer surface of the pair of side panels thereof; a U-shaped outer boot portion positioned over the lower portion of the leg at a back portion thereof, the outer boot portion having a back panel with a pair of side panels extending from the back panel along side edges thereof, the back panel and the a pair of side panels of the outer boot portion being of a material having the qualities of leather, the pair of side panels of the outer boot portion overlapping the pair of side panels of the inner boot portion and being lined with a fabric portion of the touch fastener material in releasable engagement with the hook portion of the touch fastener material on the outer surface of the pair of side panels of the inner boot portion; a plurality of pockets each having a first hook portion of the touch fastener material on a surface thereof releasably attached to the fabric portion of the touch fastener material at a point where heat or cold is to be applied to the lower portion of the leg, each pocket having a closing flap with a second hook portion of the touch fastener material on a surface thereof in common with the first hook portion when the closing flap is in a closed position; and, a plurality of gel-filled hot/cold packs disposed within respective ones of the pockets.

The lower portion 10 of the leg of a horse as depicted in FIG. 1 is prone to various problems of the muscles, joints, tendons, etc. Quite often, the lower portion 10 is wrapped with a bandage material to provide support. More recently, neoprene wraps 12 as depicted in FIGS. 2 and 3 have been employed. The neoprene wrap 12 is wrapped around the lower portion 10 and held by tabs 14 containing the hook portion 16 of touch fastener material (such as that sold under the trademark Velcro) gripping the fabric portion 18 on the outer surface of the neoprene wrap 12.

As with humans, it is often beneficial to apply heat or cold to the lower portion 10 in addition to wrapping it for support. In the past, this has been done by holding hot or cold packs in place with a wrapping bandage. More recently, a company called Professional's Choice Sports Medicine Company, Inc. has introduced a neoprene type wrap 12' as depicted in FIG. 4 provided with pockets 20 into which ice can be inserted to make what they refer to as an "ice boot" for the lower portion 10.

As can be appreciated, both the wrapping bandage and the neoprene type wrap 12' of FIG. 4 are only stop-gap measures. Both can apply excessive pressure to the lower portion 10. For example, when ice is placed into the pockets 20 of the ice boot of FIG. 4, the elastic action of the neoprene can force ice lumps of odd size and shape into the surface of the lower portion 10. Neither the wrapping bandage or the neoprene type wrap 12' of FIG. 4 provide any real protection for the lower portion 10 from outside blows. In the event that the problem being treated has rendered the lower portion 10 sensitive (which is often the case), minor blows to the wrapping bandage or the neoprene type wrap 12' of FIG. 4 can be quite painful to the horse. While the wrapping bandage can be employed to position hot or cold packs where desired, the applying and changing of the wrapping bandage can be an annoyance. The neoprene type wrap 12' of FIG. 4 is easier to put on and take off; but, can only apply ice where the pockets are located.

Wherefore, it is an object of the present invention to provide a boot for the lower portion of the leg of a horse which can be used to apply heat or cold thereto.

It is another object of the present invention to provide a boot for the lower portion of the leg of a horse for applying heat or cold thereto which is easy to put on and take off.

It is still another object of the present invention to provide a boot for the lower portion of the leg of a horse for applying heat or cold thereto where the heat or cold can be applied where desired.

It is yet another object of the present invention to provide a boot for the lower portion of the leg of a horse for applying heat or cold thereto which does not apply excess pressure to the lower portion of the leg.

It is a further object of the present invention to provide a boot for the lower portion of the leg of a horse for applying heat or cold thereto which automatically adjusts to different sized legs.

It is a still further object of the present invention to provide a boot for the lower portion of the leg of a horse for applying heat or cold thereto which provides protection against blows to the leg.

Other objects and benefits of the invention will become apparent from the detailed description which follows hereinafter when taken in conjunction with the drawing figures which accompany it.

SUMMARY

The foregoing objects have been achieved by the boot system of the present invention for selectively applying heat or cold to the lower portion of the leg of a horse for therapeutic purposes comprising, a U-shaped inner boot portion positioned over the lower portion of the leg at a front portion thereof, the inner boot portion having a front panel with a pair of side panels extending from the front panel along side edges thereof, the inner boot portion being lined with a fabric portion of a touch fastener material; a U-shaped outer boot portion positioned over the lower portion of the leg at a back portion thereof, the outer boot portion having a back panel with a pair of side panels extending from the back panel along side edges thereof, the pair of side panels of the outer boot portion overlapping the pair of side panels of the inner boot portion, the outer boot portion being lined with a fabric portion of the touch fastener material; a pocket releasably attached to the fabric portion of the touch fastener material at a point where heat or cold is to be applied to the lower portion of the leg; a gel-filled hot/cold pack disposed within the pocket; and, fastening means for holding the pair of side panels of the outer boot portion overlapping the pair of side panels of the inner boot portion.

In the preferred embodiment, the pocket has a first hook portion of the touch fastener material on one surface thereof for attaching to the fabric portion. Also, the pocket has a closing flap with a second hook portion of the touch fastener material on a surface thereof in common with the first hook portion when the closing flap is in a closed position.

The preferred fastening means comprises a touch fastener material wherein a hook portion of a touch fastener material disposed on an outer surface of the pair of side panels of the inner boot portion and a fabric portion of the touch fastener material disposed on an inner surface of the pair of side panels of the outer boot portion.

Preferably, the pair of side panels of the outer boot portion, the front panel, and the back panel all comprise a material having the qualities of leather.

DESCRIPTION OF THE DRAWINGS

FIG. 1 is a simplified drawing of the lower portion of a horse's leg.

FIG. 2 is a simplified drawing of a prior art wrap for the lower portion of a horse's leg positioned for application.

FIG. 3 is a simplified drawing of the prior art wrap of FIG. 2 after application to the lower portion of the horse's leg.

FIG. 4 is a simplified drawing of a prior art wrap such as that of FIG. 2 with the addition of pockets for holding ice therein.

FIG. 5 is a simplified drawing of the elements of a therapeutic boot system according to the present invention.

FIG. 6 is a simplified drawing showing the two boot portions of the therapeutic boot system of FIG. 5 positioned for application.

FIG. 7 is a simplified drawing showing the inner boot portion of the therapeutic boot system of FIG. 5 applied to the lower portion of the horse's leg.

FIG. 8 is a simplified drawing showing the outer boot portion positioned over the inner boot portion of the therapeutic boot system of FIG. 5 applied to the lower portion of the horse's leg.

FIG. 9 is a simplified plan view drawing of the outer boot portion of the therapeutic boot system of FIG. 5 unfolded and flattened.

FIG. 10 is a simplified plan view drawing of the inner boot portion of the therapeutic boot system of FIG. 5 unfolded and flattened.

FIG. 11 is a greatly simplified top end view drawing showing the outer boot portion positioned over the inner boot portion of the therapeutic boot system of FIG. 5 around the lower portion of the horse's leg.

FIG. 12 is a greatly simplified end view of the outer boot portion of FIG. 9.

FIG. 13 is a greatly simplified end view of the inner boot portion of FIG. 10.

FIG. 14 is a greatly simplified cutaway side view of a thermal pack pocket as employed in the therapeutic boot system of FIG. 5.

DESCRIPTION OF THE PREFERRED EMBODIMENT:

FIG. 5 is a simplified drawing of the elements of a therapeutic boot system 22 according to the present invention. The system 22 comprises an inner boot portion 24 and an outer boot portion 26. As will be seen in greater detail shortly, the inner boot portion 24 and the outer boot portion 26 are generally U-shaped and releasably connect together with touch fastener material. There are also a plurality of pockets 28 into which hot/cold packs 30 can be inserted. The pockets 28 are covered with touch fastener material as is the inside of the inner boot portion 24 and the outer boot portion 26 so that the pockets 28 can be releasably attached wherever it is desired to apply heat or cold to the lower portion 10 of the horse's leg. The preferred medium for the hot/cold packs 30 containing the heat or cold is a gel-filled flexible plastic pouch of the type commercially available from Safe & Warm Incorporated as stock number 304sw. The pouch can be placed in a freezer to cool the gel for applying cold or a disk within the gel can be flexed to cause the gel to become warm for applying heat. The pouch is then placed in a pocket 28 and the pocket 28 is attached to the inside of the inner boot portion 24 or the outer boot portion 26 where heat or cold is desired. The gel remains safely pliable whether hot or cold and retains the heat or cold for a reasonably long period of time—particularly within the closed boot 38 formed by the inner boot portion 24 and the outer boot portion 26.

As best depicted in FIGS. 9, 10, 12, and 13, the inner boot portion 24 and the outer boot portion 26 both have a thick piece of unbroken loop nylon material 32 as the entire inner surface when folded over in a squared-off U-shape as depicted in the simplified drawing of FIG. 11. The material 32 provides padding and insulation as well as acting as the fabric portion 18 of a touch fastener material. The outer boot portion 26 is covered by three pieces of heavy leather 34 forming a back and two sides which are stitched to the material 32. As can be seen from the drawing figures, since it is intended to fit over the back portion of the leg, the leather 34 is stitched together to more closely approximate the shape of the horse's leg just above the hoof and clearance is provided at the front and back to prevent chafing contact. The leather 34 provides protection from blows and also causes the outer boot portion 26 to fold at the stitching 36 to form the desired squared-off U-shape. The inner boot portion 24 has a single piece of leather 34 stitched to the material 32 at the front with panels of the hook portion 16 of a touch fastener material stitched to the material 32 on opposite sides of the single piece of leather 34. A heavy vinyl or other material having the qualities of leather could, of course, be substituted for the leather.

As depicted in FIGS. 6, 7, 8, and 11, the inner boot portion 24 folded over in its U-shape is first placed over the lower portion 10 of the horse's leg. The outer boot portion 26 is then placed over the lower portion 10 of the horse's leg and the inner boot portion 24 from the opposite direction to form a closed boot 38 around the lower portion 10 of the horse's leg. When placing the outer boot portion 26 over the lower portion 10 of the horse's leg and the inner boot portion 24, the side pieces 40 should be spread outward until the outer boot portion 26 is in position and then the side pieces 40 are pushed inward as indicated by the arrows 42 in FIG. 11 so as to engage the hook portion 16 on the sides of the inner boot portion 24. While not specifically depicted in the drawings, those skilled in the art will undoubtedly have recognized and appreciated that the boot 38 formed from the outer boot portion 26 and the inner boot portion 24 in combination automatically adjusts to different sized horse legs. For thin legs from side to side, the outer boot portion 26 and the inner boot portion 24 simply fold flatter to form a flatter U-shape. For thick legs from front to back, the outer boot portion 26 and the inner boot portion 24 simply have less overlap on the sides.

The preferred construction for the pockets 28 is depicted in simplified form in FIG. 14. In this regard, it should be noted that the drawing figures herein are not to scale in order that the details of the materials can be made more apparent. Each pocket 28 has a cloth front panel 44 and a cloth back panel 46. Both panels 44, 46 are rectangular and the back panel 46 is longer at the top to form a closing flap 48. The panels 44, 46 are stitched together along their bottom and side edges to form an enclosure 50 into which one of the hot/cold packs 30 can be inserted. The inside of the closing flap 48 has the fabric portion 18 of a touch fastener material stitched thereto while the outside of the closing flap 48 has the hook portion 16 of a touch fastener material stitched thereto. The hook portion 16 is also stitched over the cloth front panel 44. Thus, when a hot/cold pack 30 is inserted into the enclosure 50 and the closing flap 48 is folded over the opening to the enclosure 50, the fabric portion 18 of the closing flap 48 engages the hook portion 16 of the cloth front panel 44 tightly closing the enclosure 50 so that the pocket 28 has the hook portion 16 of a touch fastener material on one side for fastening to the fabric portion 18 of a touch fastener material on the inside of the outer boot portion 26 and the inner boot portion 24. According to this construction, the other side of the pocket 28 in contact with the lower portion 10 of the horse's leg is the soft cloth of the back panel 46 so as to prevent any potential for chafing.

While not preferred, the outer boot portion 26 and the inner boot portion 24 could be held together in overlapped relationship around the lower portion 10 of the horse's leg employing a wrapping bandage material instead of the touch fastener material within the scope and spirit of the present invention and such an embodiment is to be included within the protection afforded by the appended claims.

Thus, it can be seen from the foregoing description and the drawing which accompany it that the present invention has truly met its stated objectives by providing a way of safely and effectively applying heat or cold to the lower portion of the leg of a horse for therapeutic purposes.

Wherefore, having thus described the invention, what is claimed is:

1. A boot system for selectively applying heat or cold to the lower portion of the leg of a horse for therapeutic purposes comprising:
   a) a U-shaped inner boot portion adapted to be positioned over the lower portion of the leg at a front portion thereof, said inner boot portion having a front panel with a first pair of side panels extending from said front panel along side edges thereof, said inner boot portion being lined with a first fabric portion of a touch fastener material;
   b) a U-shaped outer boot portion adapted to be positioned over the lower portion of the leg at a back portion thereof, said outer boot portion having a back panel with a second pair of side panels extending from said back panel along side edges thereof, said pair of side panels of said outer boot portion overlapping said pair of side panels of said inner boot portion, said outer boot portion being lined with a second fabric portion of touch fastener material;
   c) a pocket releasably attached to said first or second fabric portion of touch fastener material at a point where heat or cold is to be applied to the lower portion of the leg;
   d) a gel-filled hot/cold pack disposed within said pocket; and,
   e) fastening means for holding said pair of side panels of said outer boot portion overlapping said pair of side panels of said inner boot portion.

2. The boot system for selectively applying heat or cold to the lower portion of the leg of a horse for therapeutic purposes of claim 1 wherein:
   said pocket has a first hook portion of touch fastener material on one surface thereof for attaching to said first or second fabric portion.

3. The boot system for selectively applying heat or cold to the lower portion of the leg of a horse for therapeutic purposes of claim 2 wherein:
   said pocket has a closing flap with a second hook portion of touch fastener material on a surface thereof in common with said first hook portion when said closing flap is in a closed position.

4. The boot system for selectively applying heat or cold to the lower portion of the leg of a horse for therapeutic purposes of claim 1 wherein:
   said fastening means comprises a touch fastener material.

5. The boot system for selectively applying heat or cold to the lower portion of the leg of a horse for therapeutic purposes of claim 1 wherein said fastening means comprises:
   a) a hook portion of a touch fastener material disposed on an outer surface of said pair of side panels of said inner boot portion; and,
   b) a fabric portion of touch fastener material disposed on an inner surface of said pair of side panels of said outer boot portion.

6. The boot system for selectively applying heat or cold to the lower portion of the leg of a horse for therapeutic purposes of claim 1 wherein:
   said pair of side panels of said outer boot portion, said front panel, and said back panel all comprise a material having the qualities of leather.

7. A boot system for selectively applying heat or cold to the lower portion of the leg of a horse for therapeutic purposes comprising:
   a) a U-shaped inner boot portion adapted to be positioned over the lower portion of the leg at a front portion thereof, said inner boot portion having a front panel of a material having the qualities of leather with a first pair of side panels extending from said front panel along side edges thereof, said inner boot portion being lined with a first fabric portion of a touch fastener material, said inner boot portion having a first hook portion of touch fastener material on an outer surface of said pair of side panels thereof;
   b) a U-shaped outer boot portion adapted to be positioned over the lower portion of the leg at a back portion thereof, said outer boot portion having a back panel with a second pair of side panels extending from said back panel along side edges thereof, said back panel and said a pair of side panels of said outer boot portion being of a material having the qualities of leather, said pair of side panels of said outer boot portion overlapping said pair of side panels of said inner boot portion and being lined with a second fabric portion of touch fastener material in releasable engagement with said first hook portion of touch fastener material on said outer surface of said pair of side panels of said inner boot portion;

c) a pocket having a second hook portion of touch fastener material on a surface thereof releasably attached to said first or second fabric portion of touch fastener material at a point where heat or cold is to be applied to the lower portion of the leg; and, d) a gel-filled hot/cold pack disposed within said pocket.

8. The boot system for selectively applying heat or cold to the lower portion of the leg of a horse for therapeutic purposes of claim 7 wherein:

said pocket has a closing flap with a third hook portion of touch fastener material on a surface thereof in common with said second hook portion when said closing flap is in a closed position.

9. A boot system for selectively applying heat or cold to the lower portion of the leg of a horse for therapeutic purposes comprising:

a) a U-shaped inner boot portion adapted to be positioned over the lower portion of the leg at a front portion thereof, said inner boot portion having a front panel of a material having the qualities of leather with a first pair of side panels extending from said front panel along side edges thereof, said inner boot portion being lined with a first fabric portion of a touch fastener material, said inner boot portion having a first hook portion of touch fastener material on an outer surface of said pair of side panels thereof;

b) a U-shaped outer boot portion adapted to be positioned over the lower portion of the leg at a back portion thereof, said outer boot portion having a back panel with a second pair of side panels extending from said back panel along side edges thereof, said back panel and said a pair of side panels of said outer boot portion being of a material having the qualities of leather, said pair of side panels of said outer boot portion overlapping said pair of side panels of said inner boot portion and being lined with a second fabric portion of touch fastener material in releasable engagement with said first hook portion of touch fastener material on said outer surface of said pair of side panels of said inner boot portion;

c) a plurality of pockets each having a second hook portion of touch fastener material on a surface thereof releasably attached to said first or second fabric portion of touch fastener material at a point where heat or cold is to be applied to the lower portion of the leg, each said pocket having a closing flap with a third hook portion of touch fastener material on a surface thereof in common with said second hook portion when said closing flap is in a closed position; and, d) a plurality of gel-filled hot/cold packs disposed within respective ones of said pockets.

* * * * *